United States Patent
Roersma et al.

(10) Patent No.: US 9,132,279 B2
(45) Date of Patent: Sep. 15, 2015

(54) DEVICE AND METHOD FOR LOW INTENSITY OPTICAL HAIR GROWTH CONTROL

(75) Inventors: Michiel Errit Roersma, Eindhoven (NL); Antonius Maarten Nuijs, Eindhoven (NL); Guido Francesco Roosen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1966 days.

(21) Appl. No.: 10/568,473
(22) PCT Filed: Aug. 5, 2004
(86) PCT No.: PCT/IB2004/051395
§ 371 (c)(1), (2), (4) Date: Feb. 15, 2006
(87) PCT Pub. No.: WO2005/016453
PCT Pub. Date: Feb. 24, 2005

(65) Prior Publication Data
US 2006/0247740 A1 Nov. 2, 2006

(30) Foreign Application Priority Data
Aug. 18, 2003 (EP) .................................... 03102582

(51) Int. Cl.
*A61B 18/18* (2006.01)
*A61N 5/06* (2006.01)
(Continued)

(52) U.S. Cl.
CPC .............. *A61N 5/0617* (2013.01); *A61B 18/203* (2013.01); *A61B 2018/00452* (2013.01); *A61B 2018/00476* (2013.01); *A61B 2018/1807* (2013.01); *A61N 2005/0659* (2013.01)

(58) Field of Classification Search
CPC ...... A61B 18/18; A61B 18/20; A61B 18/203; A61B 17/00; A61B 2018/00452; A61B 2018/0047; A61B 2017/00022; A61B 2017/00747; A61N 5/06; A61N 5/0616; A61N 5/0617

USPC ...................... 128/898; 606/2–19; 607/88–94
See application file for complete search history.

(56) References Cited

U.S. PATENT DOCUMENTS 5,059,192 A * 10/1991 Zaias ................................ 606/9
5,628,744 A * 5/1997 Coleman et al. ................ 606/12
(Continued)

FOREIGN PATENT DOCUMENTS

EP 0736308 A2 3/1996
JP 3066387 A1 3/1991
(Continued)

OTHER PUBLICATIONS

Laser hair removal, Richard J. Ort, Christine Dierickx; Seminars in Cutaneous Medicine and Surgery, vol. 21, Issue 2, Jun. 2002, pp. 129-144.*
(Continued)

*Primary Examiner* — Ahmed Farah

(57) ABSTRACT

The present invention discloses a method for controlling growth of hair on human skin with low doses of electromagnetic radiation, and a device (1) for carrying out the method. In the method, radiation (13) of a suitable spectrum is applied to the skin (12), in one or more pulses of between 1 and 100 ms, and with maximum fluencies on the skin between 1 and 12 J/cm2. By applying such low fluencies and at controlled pulse durations, follicles of the hairs are induced to the catagen phase. This means that the growth of the hairs of those follicles will stop. Although the method is not primarily aimed at immediate hair removal, hairs may be shed subsequently. In any case, further growth may be stopped for prolonged periods of time. The main advantage of the method is that the risk of damage to the skin is minimized.

14 Claims, 1 Drawing Sheet

(51) Int. Cl.
    *A61B 18/20*     (2006.01)
    *A61B 18/00*     (2006.01)

(56) References Cited

U.S. PATENT DOCUMENTS

| | | | | |
|---|---|---|---|---|
| 5,725,522 | A * | 3/1998 | Sinofsky | 606/8 |
| 5,752,948 | A * | 5/1998 | Tankovich et al. | 606/9 |
| 5,871,480 | A * | 2/1999 | Tankovich | 606/9 |
| 5,885,273 | A | 3/1999 | Eckhouse | |
| 6,080,146 | A * | 6/2000 | Altshuler et al. | 606/9 |
| 6,080,147 | A * | 6/2000 | Tobinick | 606/9 |
| 6,090,101 | A * | 7/2000 | Quon et al. | 606/9 |
| 6,214,034 | B1 * | 4/2001 | Azar | 607/89 |
| 6,273,884 | B1 | 8/2001 | Altshuler | |
| 6,436,127 | B1 * | 8/2002 | Anderson et al. | 607/89 |
| 6,579,283 | B1 | 6/2003 | Tobinick | |
| 6,595,985 | B1 * | 7/2003 | Tobinick | 606/9 |
| 6,641,578 | B2 | 11/2003 | Mukai | |
| 6,824,542 | B2 * | 11/2004 | Jay | 606/9 |
| 6,984,228 | B2 * | 1/2006 | Anderson et al. | 606/9 |
| 7,097,656 | B1 | 8/2006 | Akopov et al. | 607/90 |
| 7,217,266 | B2 * | 5/2007 | Anderson et al. | 606/12 |
| 2002/0173782 | A1 * | 11/2002 | Cense et al. | 606/9 |
| 2003/0032950 | A1 * | 2/2003 | Altshuler et al. | 606/9 |
| 2003/0065314 | A1 * | 4/2003 | Altshuler et al. | 606/9 |
| 2003/0069567 | A1 * | 4/2003 | Eckhouse et al. | 606/9 |
| 2004/0034319 | A1 * | 2/2004 | Anderson et al. | 604/20 |
| 2004/0064167 | A1 * | 4/2004 | Berry et al. | 607/89 |
| 2004/0147985 | A1 * | 7/2004 | MacFarland et al. | 607/90 |
| 2005/0177032 | A1 * | 8/2005 | Grossinger et al. | 600/310 |
| 2006/0247740 | A1 | 11/2006 | Roersma | |

FOREIGN PATENT DOCUMENTS

| | | |
|---|---|---|
| WO | 9728752 A1 | 8/1997 |
| WO | WO 98/24507 | 6/1998 |
| WO | 2005016453 A1 | 2/2005 |

OTHER PUBLICATIONS

Optical hair removal, Richard J. Ort, R. Rox Anderson; Seminars in Cutaneous Medicine and Surgery, vol. 18, Issue 2, Jun. 1999, pp. 149-158.*

Methods of hair removal, Elise A. Olsen; Journal of the American Academy of Dermatology, vol. 40, Issue 2, Feb. 1999, pp. 143-155.*

Christine Dierickx, MD, "Laser-Assisted Hair Removal" eMEDICINE, pp. 1-12.

HTTP://www.shorelaser.com/aboutlasersdet.HTML, Shore Laser Center, pp. 1-12.

R.A. Weiss, Weiss, M.A., Marwaha S. Harrington A.C., "Hair Removal With a Non Coherent Filtered Flashlamp Intense Pulsed Light Source", Lasers Surg Med 1999; 24(2). Hairfacts. HTTP://hairfacts.com/medpubs/flashlmp/weiss.HTML, pp. 1-2.

* cited by examiner

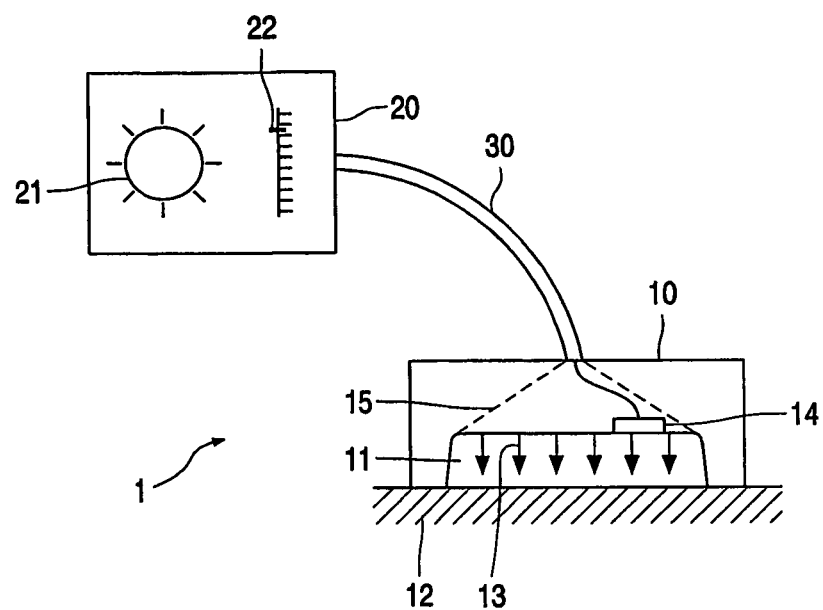

DEVICE AND METHOD FOR LOW INTENSITY OPTICAL HAIR GROWTH CONTROL

The present invention relates to a device for reducing growth of hairs on human skin, which device comprises a source of electromagnetic radiation that emits in a wavelength range between 550 and 1200 nm.

The invention also relates to a method for reducing growth of hairs on human skin, comprising delivering at least one pulse of electromagnetic radiation to the skin, wherein a wavelength spectrum of the electromagnetic radiation is selected between 550 and 1200 nm.

In the state of the art it is known to use electromagnetic radiation to remove hairs from the human skin. This is called photoepilation. Almost all of the known methods and apparatus obtain photoepilation by delivering an amount of energy to the follicles of the hairs which is sufficient to induce permanent damage to the follicles. This damage may be caused either by heating the follicles, or at least radiation absorbing particles in or near the follicles, e.g. chromophores such as melanin, to a sufficient temperature, or by providing a power density which is sufficient for such particles to explode and inflict mechanical damage on the follicles. This damage to the follicles will cause the hairs to be shed, within a short time after the treatment. Hair regrowth may be prevented for a prolonged period of time.

However, these known methods of photoepilation are rather painful, and may cause skin burns and other side effects, and inherently damage tissue in that follicles are to be damaged. A main reason therefor is the use of high energy densities of up to 40 J/cm$^2$ at the surface of the skin. Hence methods have been proposed with a lower energy load on the skin, which would therefore be less painful.

WO-98/24507 proposes a two-step method to remove hair, comprising a first step to induce synchronized growth of hairs, which is to be followed by a second step of other hair removal procedures. Firstly, hairs are synchronized in the late telogen phase/early anagen phase by irritating or slightly damaging the hair follicles so as to stimulate hairs in the skin section that are in the catagen or telogen phase to shift to the anagen phase of the hair growth cycle. The irritation or damage must not be sufficient to cause hair follicles in the anagen phase to be shifted to an inactive state. Alternatively, a radiation treatment can be used to shock anagen phase hair follicles into the telogen phase while stimulating the resting cells to transition into the anagen phase, thus synchronizing the hair cell growth. The goal of this treatment is to bring the hair follicles from an inactive into an active growth phase, while they are still in a shallow position in the skin, at a depth of about 1-2 mm, which differs from the 3-5 mm in the mature anagen phase. All this makes the follicles more vulnerable to a subsequent normal photoepilation treatment.

A disadvantage of the known method is that short pulses, in particular laser pulses, are supplied. Nothing more specific is said, but short pulses entail the risk of supplying a too high power density of radiation energy. Furthermore, the known method is to be followed by a second step of the factual hair removal, the preferred method being photoepilation. Hence the skin will subsequently be subjected to even more radiation, which may cause even more damage to tissue. Another disadvantage of the known method is that a person being treated has to wait a period of time after the synchronizing step, in order for the phase shift in the growth cycle to occur and to make the subsequent treatment more efficient. This waiting period is between 3 and 25 days. This means that the complete two-step treatment will take at least said 3 days, i.e. it can never be performed in one day, at one sitting.

WO-A-03/077783 discloses a method and apparatus for hair growth management by applying a relatively low dose of optical radiation energy to a treatment area of a patient's skin. The energy dose is sufficient to at least traumatize a matrix portion of each follicle being treated, but not to cause either necrosis of most of each said follicle or immediate gross alteration of any hair shaft therein. The treatments are preferably performed a plurality of times at selected time intervals to achieve a desired level of temporary hair growth reduction. A disadvantage of this known method and apparatus is that the method and apparatus are not sufficiently effective over their entire parameter ranges.

An object of the present invention is to provide a device and a method for reducing growth of hairs on human skin of the kinds mentioned in the opening paragraphs, which are safe and efficient, which cause as little damage to skin tissue as possible, and by which the envisaged treatment of the skin can be performed by means of only one type of treatment.

In order to achieve this object, a device for reducing growth of hairs on human skin in accordance with the invention is characterized in that the device comprises control means for limiting the deliverable energy density of the radiation on the skin to a maximum value between 1 and 12 J/cm$^2$.

In order to achieve this object, a method for reducing growth of hairs on human skin in accordance with the invention is characterized in that the energy density of the electromagnetic radiation delivered to the skin is selected to be between 1 and 12 J/cm$^2$, preferably between 5 and 9 J/cm$^2$, wherein the duration of the pulse is between 1 and 100 ms, preferably between 1 and 30 ms, such that anagen follicles of said hairs are induced to a resting phase in their growth cycle, thereby substantially preventing permanent damage to follicles of the hairs.

With the device and method according to the invention, use is made of the insight that it is advantageous to stimulate the anagen hair follicles to switch to a telogen, or resting phase, or inactive phase. It was found that an appropriate combination of pulse time and low energy densities of the radiation may bring about said transition to the resting phase, in order to thereby control hair growth on the skin and obtain an efficient degree of temporary hair growth reduction. Moreover, because of the selected combination of pulse time and low energy densities, pain and other discomfort to the person being treated is minimal. In particular the chance of tissue being damaged is reduced to a minimum.

Although it is not a principal aim of the present invention to remove the hairs at once by applying the method, it may in fact have this result. This will be elucidated further hereinbelow. The main consideration is that hairs of a person that no longer grow will limit discomfort to the person, especially perceptual/cosmetic discomfort, i.e. limit the displeasing appearance of hairy skin, as well as an unwanted rough skin. If treated soon enough, the person will experience no or only very little discomfort from said hairs.

A particular embodiment of a device according to the invention is characterized in that, during operation, the control means limits the deliverable energy density of the radiation on the skin to a maximum value between 5 and 9 J/cm$^2$. A high efficiency is obtained, while the risks of tissue damage are still kept low.

A particular embodiment of a device according to the invention is characterized in that, during operation, the control means selects the maximum value in accordance with selected properties of the skin to be treated. Said selected properties may be skin color and color of the hairs to be treated. This offers the advantage of achieving maximum efficiency with minimum risk of tissue damage. Said maximum value of the energy density delivered to the skin may be adjustable, for instance by a dermatologist, who may assess whether for example the color of the skin of a person being treated has changed (such as is caused by tanning). Furthermore, said maximum value may be selectable from a number of preset values, in order to allow the device to be used by or for persons with different requirements. A maximum value selection knob may be provided for that purpose. For example, for a person with dark hairs but a light-colored skin, a higher energy density may be selected than in the case of a dark skin and pale hairs.

A particular embodiment of a device according to the invention is characterized in that the wavelength range is between 600 and 950 nm. A particular embodiment of a method according to the invention is characterized in that the wavelength spectrum is between 600 and 950 nm. For these wavelengths, there is a good absorption by elements of the follicle to be stimulated, such as melanin bodies. Advantageously, the wavelength range is adapted to the skin type and hair color of the person being treated. Different skin types may need a different approach. For instance, it is preferable to use longer wavelengths, such as short wave infrared from about 800 to about 1200 nm, for persons with a dark skin, in order to prevent too much absorption by melanin in the skin, which is undesirable.

It is noted that the radiation may be continuous spectrum radiation, line spectrum radiation, monochromatic radiation, or a combination thereof. This also holds for the general range of 550-1200 nm. It must also be stressed that the actually emitted radiation may comprise other parts of the spectrum, but that it should emit at least in the indicated wavelength region.

Advantageously, in a device according to the invention the source is a pulsed source that emits radiation pulses with a duration between 1 and 100 ms. A particular embodiment of a device according to the invention is characterized in that the duration of the radiation pulses is between 1 and 30 ms. A preferred embodiment of a device according to the invention is characterized in that the duration of the radiation pulses is between 10 and 20 ms. A correct duration is important to prevent a too high power density in and on the skin, as a too high power density could cause tissue damage because of too quick or even violent heating of (parts of) tissue. A relatively long pulse duration limits the risk of tissue damage. However, a too long pulse duration would limit the efficiency of the device. Good results are obtained with the preferred pulse duration, although other pulse durations are not to be excluded. With the preferred pulse duration the degree of thermal diffusion to the tissue surrounding the hair follicles is relatively low. As a result, most of the energy absorbed by the hair follicles will remain in the hair follicles, so that the absorbed energy is used as efficiently as possible in obtaining the desired effect of hair growth reduction, and the required energy density can be as small as possible.

In an advantageous embodiment of a device according to the invention, the pulse is obtained by moving a source of the electromagnetic radiation. This means that a certain area of the skin will be irradiated only during the time needed for a source of radiation, used in the device, to pass said area. This time is called the dwell time. This may be considered as one single pulse. Of course it is also possible to obtain a pulse by the controlled switching of a source of radiation. Likewise, more than one pulse may be generated.

In an even more advantageous embodiment of a device according to the invention, a velocity of the source and a power density of the radiation emitted by the source are selected such that the energy density of the radiation delivered to the skin is between 5 and 9 J/cm$^2$. In this embodiment, the energy density of the radiation delivered to the skin is the mathematical product of the dwell time and the power density of the radiation emitted by the source. The selection of the velocity of the source will be made by the operator of the device, in accordance with instructions and with the selected power density of the source. It is to be understood that in this context 'source' means the part of a device that actually emits the radiation, whereas sometimes a distinction is made between the source as a part that generates the radiation and e.g. a treatment head that emits the radiation. It will always be clear what part is meant.

Preferably, the velocity of the source is measured, and the emitted power density is selected in dependence on said velocity, such that the energy density delivered to the skin is between 5 and 9 J/cm$^2$. In this way it is ensured that the treated skin will not be overexposed to the radiation. The power density emitted by the source may be adapted to the actually selected velocity with which the source, or more precisely the treatment head, is being moved across the skin. Since this velocity will not always be constant, the power density emitted by the source also should not be constant, but adapted to the actual speed.

A particular embodiment of a device according to the invention is characterized in that the source is a continuous source, the control means being designed to measure a velocity with which the device is moved over the skin to be treated and to adjust the energy density of the radiation emitted by the source as a function of the measured velocity, such that the energy density of the radiation delivered to an area of the skin being treated is at most equal to the maximum value. Although it is not strictly necessary to measure said velocity, it will help in limiting the energy density emitted by the source to the maximum value. In particular, if the device is moved with a velocity v, and if an emission window of the device, that emits the radiation, has a dimension d in the direction of movement over the device, then a dwell time $t_D$ may be defined as $t_D=d/v$. The dwell time is equal to the time during which an area of the skin is being irradiated. Assuming that the power density of the radiation emitted by the source has a constant value, both over the emission window and in time, then the energy density becomes equal to the mathematical product of said power density and said dwell time. The control means in this embodiment are designed to adapt the power density emitted by the source in order for the energy density to remain below the selected maximum value. To this end, the control means may, for example, comprise attenuation means, such as two adjustable polarizers, or they may be designed to adjust the power supplied to the source.

A particular embodiment of a device according to the invention is characterized in that the source comprises a flash lamp. A flash lamp is a simple and small broad band source, that can be controlled very easily by setting released energy and/or flash time. In particular, such a flash lamp is much smaller and more convenient than a laser. Furthermore, a laser is also subject to stringent regulations, which makes a laser less suitable to be used as a source by unskilled persons at home.

Further objects, features and advantages of the invention will be understood more clearly by reading the following description of preferred embodiments.

The device for reducing growth of hairs on human skin according to the invention may be embodied like a known apparatus, and further comprise appropriate control means. These control means may comprise a small computer or comparable means.

In particular, the device may comprise a source of electromagnetic radiation, such as a flash lamp or halogen lamp. In this case, the source may comprise a filter for filtering out unwanted radiation, such as ultraviolet radiation. The device may emit the generated radiation through an emission window, which may consist of an opening in the device, or may comprise a piece of transparent material. Preferably, the emission window is cooled, e.g. a cooled sapphire window.

The device may further comprise velocity measuring means for measuring the velocity with which the device, and notably the emission window, is moved across the skin. The control means are then designed such that they can process the measured velocity in order to set the emitted power density to a value that allows the energy density that is received by the skin to remain below a predetermined maximum value.

The device, and in particular the control means, may further comprise selection means for selecting the maximum value, in accordance with certain biophysical properties of the skin, such as skin color. The selection means may comprise a control knob that may be moved along an indicator scale in order to set the device to the correct combination of skin properties that are indicated on the indicator scale.

Preferably, the device comprises a sensor for measuring the biophysical skin properties, such as skin color, such that the device may be set to such values of the maximum value of energy density, spectrum and/or pulse duration that give the best efficiency without inducing unwanted side-effects.

Advantageously, the device, and in particular the control means, are automated, such that the setting of the device will take place automatically after measuring the skin to be treated. This will reduce the number of errors in operating the device.

Even more advantageously, the apparatus has one fixed setting of the maximum value of energy density, spectrum and/or pulse duration. This limits the number of errors even further, in that only one kind of treatment is possible. Preferably, the fixed setting is set based on the clients wish. This setting may be fixed in the factory or by a dermatologist etc. This offers a fool-proof device which is still optimized for the specific client and his skin. Such fixed setting may however also be used more generally for people with about the same skin type, e.g. fair skin, etc.

In the method in accordance with the invention, anagen hair follicles are induced to go to a resting stage in their growth cycle, in order to thereby limit (re)growth of hair during a prolonged time, however without causing severe damage to the follicle.

Hair follicles go through the so-called hair growth cycle. A first phase in this cycle is called the anagen (growing) phase, in which the follicle produces a hair. At the end of the anagen phase the follicle switches to the catagen (intermediate) phase, which is automatically followed by the telogen (resting) phase. At the end of the telogen phase, after some time, the follicle will automatically enter the anagen phase again.

By switching the hair follicles to catagen phase and subsequently to telogen phase, by applying electromagnetic radiation to the skin with the device in accordance with the invention and in accordance with the method according to the invention, long lasting hair growth control is obtained. Since hair follicles in the telogen phase will shed their hairs, it is even possible that the hairs are removed with the method. However, this is not always the case, and will often take some time.

If such hair growth control is not sufficient, the method according to the invention may preferably be combined with other methods of hair removal, however preferably with methods that do not use electromagnetic radiation, since that would lessen the advantages of the present invention. Advantageously, the method is combined with e.g. plucking, waxing, shaving or chemical removing of the hairs. An advantage of this combination is that in effect hairs are removed, while at the same time regrowth is inhibited for a prolonged period of time. Note that plucking alone may also switch hair follicles to the catagen and then telogen phase, but plucking does not result in more than about 50% of the follicles being switched to catagen. Hence regrowth is suppressed less.

Another advantage of combining the method according to the invention with other types of epilation without radiation is that it may be performed by untrained people at home, without much risk of injury or tissue damage, and still provide even better hair growth control.

In an example of the method according to the invention, a flash lamp treatment at 9 $J/cm^2$ optical energy at skin level, 15 ms pulse duration, and 600-950 nm spectrum showed similar hair results after one treatment as a flash lamp treatment at 15 $J/cm^2$. However, the discomfort to the persons being treated was much less. Persons treated with the device using the former settings can only just feel that their skin is being treated (e.g. a warm sensation on their skin), whereas persons treated with the device using the latter settings indicate that this treatment is rather painful to their skin. Moreover, the skin treated at 9 $J/cm^2$ has a lower chance of burns, blisters, hypopigmentation, hyperpigmentation, etc. than the skin treated at 15 $J/cm^2$.

In some cases it may be that only a portion of the anagen hair follicles are induced to switch to the catagen phase, followed by the telogen phase as a result of the treatment. In this case it is beneficial to wait a certain period; e.g. 2 weeks, and then treat the same area of skin again. This should be repeated until the final result is reached. After these initial treatments, regular treatments, e.g. at 2 week intervals, are applied to maintain the hair removal result by inducing catagen, followed by telogen, to those hair follicles that have naturally switched from the telogen to the anagen phase since the last treatment and have started growing a new hair.

Using the described method (9 $J/cm^2$, 600-950 nm, 15 ms) and treatment protocol (shave and photo-epilate the skin every 2 weeks), typical results that can be reached are: 10% hair reduction 2 weeks after 1 treatment, 60% hair reduction 2 weeks after 2 treatments, and 90% hair reduction 2 weeks after 3 treatments.

The present invention will be understood more clearly after reading the following description of a preferred embodiment, in connection with the appended drawing, in which the only FIG. 1 schematically shows a device for reducing growth of hairs on human skin according to the invention.

In the FIG. 1, the device 1 comprises a treatment head 10 and a power and control unit 20, interconnected by a connecting cable 30.

A treatment cavity is denoted by 11, and is to be placed on skin 12. 13 denotes radiation, and 14 is a sensor. Dashed line 15 indicates boundaries of radiation inside the treatment head.

The power and control unit comprises first and second control knobs 21, 22 respectively.

The treatment head comprises a source (not shown) for the light 11. The source may either be present in the treatment head or outside it, e.g. in the power and control unit 20. In the latter case, the light may be transported through the connecting cable 30. The dashed lines 15 schematically indicate the boundaries of the lighting inside the treatment head 10. They may stand for the boundaries of a light bundle in the head 10, or e.g. for optical fibers that transport the light inside the head 10 towards the treatment cavity 11.

The light, or rather the radiation, that is used in the device may be any radiation according to the method of the invention. The wavelength is in the range of 550 to 1200 nm, for example yellow/red light. Suitable light sources are e.g. flash lamps, with filters, or a (pulsed) halogen lamp. The source may be powered and controlled by the power and control unit 20, although both functions may be separated if desired.

The treatment head 10 may be designed to cover an appropriate area of the skin 12. The treatment cavity 11 need not be a true cavity, but may also be covered with a transparent material, and it may also be completely absent in that the light is emitted from a surface in direct contact with the skin.

One advantage of there being a treatment cavity 11 is that a sensor 14 may be used for measuring biophysical properties of the skin 12. The sensor 14 measures for example the color and darkness of the skin 12, by analyzing the light reflected off the skin 12. The sensor 14 could also be used to determine a velocity of the treatment head 10, in order to determine the amount of released energy per skin area. However, it is also possible to use a separate sensor for one or more of these functions. Note that the sensor 14 is not at all indispensable in the device according to the invention.

The power and control unit 20 comprises first and second control knobs 21 and 22. Any other number of control knobs, such as one, three etc., and even zero, is also possible however. The latter indicates a preset device.

The first control knob 21 may be a power indicator, with which e.g. the maximum value of the energy density on the skin may be set. Typical values are for instance 4, 6 and 9 J/cm$^2$, while a range between 1 and 12 J/cm$^2$ is allowable according to the invention. The first control knob may also comprise, or be embodied as, an on-off function.

The second control knob may e.g. be a selector of the pulse time of the radiation used. Typical values for the pulse length according to the invention are between 1 and 100 ms, for instance 5, 10, 15, 20 and 30 ms.

Other possible controls include a selection of a specific spectrum by choosing an appropriate filter, or e.g. the selection of a certain user of the device. In the latter case, one knob may be used which sets all possible controls at once for the person which is to be treated. This option may for instance be useful in families, or in a dermatologist's practice.

Although the device 1 has been shown as made up of a separate treatment head 10 and power/control unit 20, it is also possible to integrate these into one unit. However, a separate treatment head has the advantage that it may be smaller and more lightweight, which improves the operation of the device. The connecting cable 30 connects the treatment head 10 to the power and control unit 20. The connecting cable 30 may comprise a power cable for the treatment head, and an optional data cable for communication with e.g. the sensor 14. It is also possible that the source of radiation is built into the power and control unit 20, and that e.g. optical fibers are used to guide the radiation to the treatment head 10. In this case the optical fibers may also be comprised in the connecting cable 30.

The device 1 as shown may be combined with any other features that do not form part of the invention, but that may be useful, such as cooling surfaces, means for removing possible debris and smells, etc.

The present invention has been illustrated by means of preferred embodiments. However, the invention is not to be construed as limited thereby. The scope of the invention is determined by the appended claims.

The invention claimed is:

1. A device for reducing growth of hairs on human skin, said device comprising:
    a source of electromagnetic radiation that emits electromagnetic radiation in a wavelength range between 550 and 1200 nm, said electromagnetic radiation being directed towards the skin,
    a sensor for analyzing a reflection, from the skin, of the emitted electromagnetic radiation in order to determine selected properties of the skin; and
    control means for:
        controlling said source of electromagnetic radiation to a maximum deliverable energy density of the electromagnetic radiation, said maximum deliverable energy density being in a range to a between 1 and 12 J/cm$^2$,
        determining a value of deliverable energy density to said skin based on said determined selected properties, said value of deliverable energy density being no greater than said maximum deliverable energy density; and
        outputting said electromagnetic radiation from said source at said determined value of deliverable energy density.

2. The device as claimed in claim 1, wherein during operation, the control means limits the deliverable energy density of the radiation on the skin to a maximum value in a range between 5 and 9 J/cm$^2$.

3. The device as claimed in claim 2, wherein the source comprises a flash lamp.

4. The device as claimed in claim 1, wherein the wavelength range is between 600 and 950 nm.

5. The device as claimed in claim 1, wherein the source is a pulsed source that emits radiation pulses with a duration between 1 and 100 ms.

6. The device as claimed in claim 5, wherein the duration of the radiation pulses is between 1 and 30 ms.

7. The device as claimed in claim 6, wherein the duration of the radiation pulses is between 10 and 20 ms.

8. The device as claimed in claim 5, wherein the source comprises a flash lamp.

9. The device as claimed in claim 1, wherein the source is a continuous source.

10. The device as claimed in claim 1, wherein said control means further comprising:
    measuring a velocity with which the device is moved over the skin, and
    adjusting the energy density of the radiation emitted by the source as a function of the measured velocity.

11. A method for reducing growth of hairs on human skin, said method comprising the steps of:
    delivering at least one pulse of electromagnetic radiation to the skin, said electromagnetic radiation having a wavelength spectrum selected between 550 and 120 nm, wherein a duration of the pulse is between 1 and 100 ms such that anagen follicles of said hairs are induced to a resting phase in their growth cycle, thereby substantially preventing permanent damage to follicles of the hairs;
    setting a maximum deliverable energy density of said source in a range between 1 and 12 J/cm$^2$;
    measuring a reflection of the electromagnetic radiation from the skin being treated, and
    determining selected properties of the skin being treated based on the measured reflection; and controlling said electromagnetic radiation to a value based on said determined selected properties, wherein said value is not greater than said maximum deliverable energy density.

12. The method as claimed in claim 11, wherein the wavelength spectrum is between 600 and 950 nm.

13. The method as claimed in claim 11, wherein the energy density of the electromagnetic radiation delivered to the skin is selected between 5 and 9 J/cm$^2$.

14. The method as claimed in claim 11, wherein the duration of the pulses is between 1 and 30 ms.

* * * * *